| United States Patent [19] | [11] Patent Number: 4,638,096 |
| Virnig | [45] Date of Patent: Jan. 20, 1987 |

[54] PROCESS OF PREPARING HYDROXYARYLALDEHYDES AND CATALYST THEREFOR

[75] Inventor: Michael J. Virnig, Fridley, Minn.

[73] Assignee: Henkel Corporation, Minneapolis, Minn.

[21] Appl. No.: 433,745

[22] Filed: Oct. 12, 1982

[51] Int. Cl.$^4$ ..................... C07C 47/565; C07C 45/45
[52] U.S. Cl. .................................. 568/433; 568/315; 502/171
[58] Field of Search ................................ 568/433, 315

[56] References Cited

U.S. PATENT DOCUMENTS 4,085,146  4/1978  Beswick .
4,151,201  4/1979  Casnati et al. .
4,324,922  4/1982  Smith .................................. 568/437

FOREIGN PATENT DOCUMENTS 0077279  4/1983  European Pat. Off. .

Primary Examiner—Bernard Helfin
Attorney, Agent, or Firm—Ernest G. Szoke; Patrick J. Span

[57] ABSTRACT

A process is disclosed for preparing hydroxyarylaldehydes wherein a corresponding phenolic compound is reacted with formaldehyde, in the presence of a titanium or zirconium containing catalyst, optionally in the presence of a catalyst promoter. Among other uses, the aldehydes are particularly useful as intermediates in the preparation of the corresponding oximes, which find utility as metal extractants.

32 Claims, No Drawings

PROCESS OF PREPARING HYDROXYARYLALDEHYDES AND CATALYST THEREFOR

BACKGROUND OF THE INVENTION

This invention relates to the preparation of hydroxyarylaldehydes wherein a corresponding phenolic compound is reacted with formaldehyde, or a formaldehyde liberating compound in the presence of a titanium or zirconium containing catalyst, particularly a titanium or zirconium (IV) catalyst Among other uses known to the art, the aldehydes are particularly useful as intermediates in the preparation of the corresponding oximes, which find utility as metal extractants.

The hydroxyarylaldehydes may be prepared by a number of routes. A summary and review of the synthesis of aromatic hydroxyaldehydes may be found in H. Fiege, K. Wedemeyer, K. A. Bauer, A Krempel and R. G. Molleken, Fragrance Flavor Subst. Proc. Int. Haarmann Reimer Symp. 2nd, 1979 (Publ. 1980), pp 63–73, which discusses in particular three processes of preparation.

One of these three processes is the Reimer-Tiemann reaction which involves the reaction of a phenol with chloroform under very basic conditions to give the salicylaldehyde. Yields tend to be low and recovery of the product difficult. A recent patent, U.S. Pat. No. 4,324,922, relates to improvements in the process citing as further background Hans Wynberg, "Chemical Reviews", Vol. 60, 169 (1960) and Ferguson, "Chemical Reviews", Vol. 38, 229 (1946). Other U.S. Pat. Nos. 3,206,513 and 3,972,945 provide further background in relation thereto.

A second industrially useful approach involves condensation of the phenol with formaldehyde followed by oxidation with oxygen and a catalyst. While reasonable yields of salicylaldehyde are obtained, the process consists of two steps and involves the use of expensive catalysts. Illustrative of some of the patents relating to this process are U.S. Pat. Nos. 3,173,956, 3,321,526, 3,673,257, 3,780,110, 4,026,950 and 4,190,605.

Two other recent variations have been introduced. The first, which can be seen in U.S. Pat. No. 4,151,201, involves heating paraformaldehyde with phenol in the presence of anhydrous stannous chloride and pyridine. The second, which can be seen in U.S. Pat. No. 4,231,967, involves replacing the stannous chloride with an iron or chromium compound, preferably chromium acetylacetonate. Good yields are obtained via both processes. Both processes require relatively high levels of pyridine, which must be recycled and requires special handling on an industrial scale. The presence of the heavy metals also presents problems in waste disposal. Further iron and chromium compounds tend to promote adverse side reactions.

Another process, which can be seen in U.S. Pat. No. 4,085,146 directed specifically towards production of alkylsalicylaldehydes, involves formation of a Mannich base, followed by oxidation and hydrolysis to the alkylsalicylaldehyde. While good yields are obtained, the process is economically burdensome due to the number of steps involved.

SUMMARY OF THE INVENTION

The present invention involves the reaction of a phenolic compound (such as an alkylphenol) with formaldehyde, or a formaldehyde liberating compound (such as paraformaldehyde) in the presence of a titanium or zirconium containing catalyst (such as a titanium or zirconium (IV) ester or complex), optionally in the presence of a catalyst promoter (such as pyridine). This process has a number of key advantages. Excellent yields are obtained in one process step. When pyridine is employed, the reaction requires less than one tenth the pyridine required with the stannous or chrome catalysts. The titanium(IV) esters useful as catalysts are cheap and readily available. The by-product from the catalyst is titanium dioxide; hence, waste disposal is greatly simplified.

DETAILED DESCRIPTION OF THE INVENTION

As indicated above, the present invention involves the preparation of aldehydes by reaction of a phenolic compound with formaldehyde in the presence of a titanium or zirconium catalyst, particularly a titanium or zirconium (IV) catalyst. The invention also relates to novel complexes useful as catalysts in the reaction.

In the present invention, the reaction temperature is desirably on the order of about 150°–250° C. Temperatures below 150° C. may be employed but this is undesirable as a long period of time would be required to complete the reaction. At temperatures above 250° C. side reaction may occur and results are poor either in yields or quality. In any event a temperature sufficiently high for the reaction of the phenolic compound and the formaldehyde within a practical time period is desired, while avoiding decomposition or adverse side reaction. The most desirable and preferred temperature range is generally found in the range of about 180°–220° C.

The process is generally carried out at greater than atmospheric pressure. About 2 hours are required for complete reaction at 180° C. with longer periods at the lower temperatures and shorter periods at higher temperatures. In general from about 0.5–8 hours is a practical time in which to carry out the reaction.

The reaction is conducted in a solvent system, utilizing conventional solvents for such reaction. The preferred solvent systems are the aromatic hydrocarbons such as toluene, benzene, xylene, chlorobenzene and isopropyl benzene; however, the aliphatic hydrocarbons and ethers, among those disclosed in U.S. Pat. No. 4,231,967, are also desirable solvents. As a practical matter any solvent system for the reactants which does not strongly coordinate with the catalyst or otherwise substantially interfere with reaction is suitable.

Under the reaction conditions of this process the preferred formaldehyde compounds to be used are formaldehyde and paraformaldehyde. The molar ratio of formaldehyde to phenolic compound is generally in the range of about 2–6:1 and preferably 3–5:1.

The phenolic compounds useful in the present process are those having an available activated or unsubstituted position adjacent the phenolic, hydroxyl group, such as the ortho position of phenol. The present process appears selective for the ortho-position with no reaction at the para-position. Thus the preferred compounds are those phenols having at least one unsubtituted ortho position available for reaction. Exemplary classes of phenolic compounds which are suitable for this invention are alkyl and aryl (including alkaryl and aralkyl) phenols, cycloalkyl phenols, alkoxy and aryloxy phenols, acyl phenols and halophenols, as well as phenol itself. Thus, many of the phenolic compounds may be such as are found in U.S. Pat. Nos. 4,324,922, 4,231,967 and 4,151,201, and for the purpose of this invention may be defined by the following structural formula:

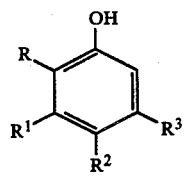

where R,R¹,R² and R³, which can be the same or different, represent hydrogen atoms, alkyl, aryl, alkaryl, aralkyl, cycloalkyl, alkoxy, aryloxy, acyl groups or halogen. In these compounds the desirable alkyl groups generally contain from about 1–22 carbon atoms and the aryl group is phenyl. For those phenolic compounds which are to be converted to the corresponding oximes for use as metal extractants, the alkyl substituted compounds in which the alkyl groups contains from 8–22 carbon atoms, and preferably the 9 and 12 carbon atom groups, are the most desirable. Other desirable substituted phenols include cresol, tert-butylphenol (ortho and para), p-cumylphenol, cyclohexylphenol, 4-methoxyphenol, and o- or p-chlorophenol.

The catalysts useful in the present invention are titanium or zirconium containing compounds and particularly titanium or zirconium (IV) compounds, or compounds in which the titanium or zirconium becomes oxidized to the (IV) state in the course of the reaction. Metallic titanium or zirconium itself is not suitable for use alone in the process. The particular catalyst employed is somewhat dependent upon the particular solvent and phenolic compound system employed in that the catalyst must be soluble in the system used to provide desirable results in yields and quality. Accordingly for the purpose of this invention, the catalyst contains an organic moiety to provide solubility in the system. The organic moiety may be introduced by preforming the catalyst to contain such moiety or by formation in situ in the course of the reaction. The examples to follow will serve to illustrate the particular systems which are preferred for use with specific catalysts.

A large number of titanium compounds are known, many of which are commercially available, at least in laboratory sample quantities. In the nomenclature of the titanium compounds strict chemical names are not always employed and common names are frequently used in combination with well established chemical nomenclature systems. Accordingly it has become common to those in the field of titanium chemistry to refer to the titanium(IV) alkoxides as alkyl titanates. Thus, titanium(IV) butoxide can also be referred to as tetrabutyl titanate or simply butyl titanate. The preferred titanium compounds (or their zirconium counterparts) are the tetra-alkyl (alkoxides) and tetra-aryl titanates, titanium acylates, titanium halides organic containing titanium oxides and chelated compounds of titanium (IV). A list of various organic titanium compounds can be found in "The Organic Chemistry of Titanium", Raoul Feld & Peter L. Cowe, Washington, Butterworths, 1965. On pages 66 and 67 thereof are disclosed several species of chelated compounds of titanium which are useful in the present process. The 8-hydroxyquinoline chelated compounds or complexes tend to provide further improvement in yield over the non-chelated. Thus, this chelated titanium ester will provide improved yield over the titanate ester itself when employed in the same system. The chelated or complex compositions found preferable in the present invention are the complexes of 2,4-pentanedionates, an 8-hydroxyquinoline complex and a salicylaldehyde (including the aldehydes formed by this invention) complex of the titanate esters. Particularly desirable are the reaction products of 8-hydroxyquinoline with titanium cresylate and titanium(IV) butoxide; the reaction products of salicylaldehyde with titanium cresylate; and titanium(IV) diisopropoxide bis(2,4-pentanedionate) and titanium(IV) oxide bis(2,4-pentanedionate). These complexes are generally preformed prior to reaction by mixing the desired titanate compound with the complexing compound for about 30 minutes. The molar ratio of catalyst to phenol is generally on the order of about 0.005 to 0.0005 and preferably in the range of 0.017 to 0.0005.

The preferred catalysts may also be represented by the formula

where M represents titanium or zirconium, any one of W,X,Y and Z may be halide (preferably Cl, I, or Br), alkoxy, aralkoxy, aryloxy, alkaryloxy, or acyloxy, cyclopentadienyl, or residues of a β-diketone, 8-hydroxyquinoline or a salicylaldehyde, and when any two of W,X,Y,Z together are oxide, the other two are selected from the group of halogen, alkoxy, aralkoxy, aryloxy, alkaryloxy, acyloxy, a β-diketone residue, (such as acetylacetone), an 8-hydroxyquinoline residue or a salicylaldehyde residue such as salicylaldehyde itself or substituted salicylaldehydes such as prepared by this invention, i.e. nonylsalicylaldehyde. Generally the alkyl portion of the alkoxy group will contain from 1 to 22 carbon atoms and the aryl portion is phenyl such as phenoxy.

Titanate polymers may also be employed as catalysts such as may be represented by the formula

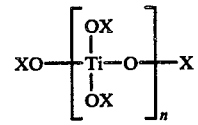

where n is an integer representing the number of repeating units and where X, which may be the same or different, is alkyl, aryl, alkaryl, or aralkyl, or a residue of a β-diketone such as acetyl acetone, or an 8-hydroxyquinoline, or a salicylaldehyde.

In order to further promote the reaction a catalyst promoter may be added to the reaction system. These generally are unhindered aromatic amines, such as pyridine or quinoline, or phosphine oxides or phosphates, such as trioctylphosphine oxide and tributylphosphate.

The invention is further illustrated, but not limited, by the following examples in which all parts and percentages are by weight unless otherwise stated.

EXAMPLES 1–14

Several preparations of nonylsalicylaldehyde (NSA) were made using different catalysts from a commercially available p-nonylphenol (in which the nonyl group is derived from propylene trimer). The procedure employed was as follows.

Toluene (750 to 850 ml.) was charged to a two liter Parr stirred autoclave, model 4500, and heated to 200° C. A slurry containing 147g. (0.668 mole) of nonylphenol, 63g.(2.0 moles @95%) of paraformaldehyde, 2.1 g. (0.026 mole) of pyridine, 50 ml. of toluene, and 0.0038 mole of the catalyst shown in Table 2 was then pumped over a period of 5-30 minutes into the reactor. An additional 100 to 200 ml. of toluene was then pumped into the reactor to insure transfer of all the reactants into the reactor. In example 2 the pyridine was charged directly to the reactor with the initial toluene. After two hours at 200° C., the reactor was cooled, and the contents transferred to a 2 liter separatory funnel. The organic phase was washed with 10gpl sulfuric acid, water washed to neutrality, and then the solvent was removed. The resultant oil was then assayed by gas chromatography.

TABLE 1

| Ex. | Catalyst | NSA Yield (%) |
|---|---|---|
| 1 | no catalyst | 11.8 |
| 2 | Titanium(IV) cresylate | 59.5 |
| 3 | Octylene glycol titanate | 58.2 |
| 4 | Triethanolamine titanate | 52.6 |
| 5 | Titanium(IV) diisopropoxide bis(2,4-pentanedionate) | 58.2 |
| 6 | Titanium(IV) oxide bis(2,4-pentanedionate) | 52.7 |
| 7 | Titanium tetrachloride | 43.0 |
| 8 | Bis(cyclopentadienyl) titanium dichloride | 55.8 |
| 9 | Isopropyl triisostearoyl titanate | 61.9 |
| 10 | Isopropyl tricumylphenyl titanate | 55.9 |
| 11 | Isopropyl tri(N—ethylamino-ethylamino) titanate | 28.2 |
| 12 | Isopropyl tri(2-aminobenzoyl)titanate | 56.7 |
| 13 | Tetraisopropyl di(dioctylphosphito) titanate | 39.0 |
| 14 | Zirconium (IV) 2,4-pentanedionate | 40.9 |

EXAMPLES 15-19

Using a slightly different procedure at a temperature of 180° C. additional runs were made employing the same nonylphenol as in the preceding examples. The procedure was as follows.

To a two liter Parr stirred autocleve, Model 4500, equipped with thermocouple were added 147g. (0.668 mole) of nonylphenol, 63g. (2.0 mole @ 95%) of paraformaldehyde, one liter of toluene, 2.1 g. (0.026 mole) of pyridine, and 0.0038 mole of a catalyst shown in Table 1. The reactor was then sealed, heated to 180° C. over a twenty minute period, and then stirred for 2 hours at 180° C. The reactor was then cooled. The reactor contents were then worked up and assayed as described for Examples 1 to 14.

The results can be seen from Table 2.

TABLE 2

| Ex. | Catalyst | NSA Yield (%) |
|---|---|---|
| 15 | Titanium(IV) cresylate | 52.1 |
| 16 | Titanium(IV) butoxide | 51.7 |
| 17 | Titanium diisopropoxide bis(2,4-pentanedionate) | 54.8 |
| 18 | Triethanolamine titanate | 50.2 |
| 19 | Zirconium(IV) butoxide | 38.7 |

EXAMPLES 20-23

Several runs were made following the same procedure as employed in Example 15, but varying the amount of pyridine. The results are shown in Table 3.

TABLE 3

| Ex. | Pyridine Weight (g) | Pyridine Mole | NSA Yield (%) |
|---|---|---|---|
| 20 | 0.00 | 0 | 48.5 |
| 21 | 0.42 | 0.005 | 52.3 |
| 22 | 2.10 | 0.026 | 53.6 |
| 23 | 21.00 | 0.16 | 53.4 |

The foregoing illustrates that while the yields are significant even without the pyridine, further improvement is possible by the use of pyridine as a catalyst promoter, even at relatively low levels of pyridine.

EXAMPLES 24 to 26

In these examples the temperature was varied to illustrate the effect thereof. Otherwise the procedure and materials were the same in Example 15. The results are as shown in Table 4.

TABLE 4

| Example | Reaction Temperature | NSA Yield (%) |
|---|---|---|
| 24 | 160° C. | 49 |
| 25 | 180° C. | 52.1 |
| 26 | 200° C. | 53.5 |

EXAMPLES 27 AND 28

These examples also illustrate the effect of higher temperatures but in this instance the procedure and materials employed were as described in Example 1. The results are shown in Table 5.

TABLE 5

| Example | Reaction Temperature | NSA Yield (%) |
|---|---|---|
| 36 | 200° C. | 59.6 |
| 37 | 225° C. | 58.0 |

EXAMPLES 29 TO 31

In these examples, the catalyst concentration was varied to illustrate the effect thereof, using the procedure and materials of Example 15. The results are shown in Table 6.

TABLE 6

| Example | Catalyst Weight (g.) | Catalyst Mole | NSA Yield (%) |
|---|---|---|---|
| 29 | 0.35 | 0.0007 | 56.5 |
| 30 | 1.80 | 0.0038 | 52.1 |
| 31 | 5.40 | 0.011 | 45.9 |

EXAMPLES 32 AND 33

In these examples the effect of differing solvent is illustrated. The procedure and materials were the same in Example 15. The results are shown in Table 7.

TABLE 7

| Example | Solvent | NSA Yield (%) |
|---|---|---|
| 32 | Toluene | 52.1 |
| 33 | Isooctane | 32.3 |

EXAMPLES 34 TO 36

In these examples the procedure was carried out in the same fashion as in Example 20 with the following modifications. The reactor was charged with 123.2g (0.56 mole) of nonylphenol, 67.3g. (2.24 moles @ 95%) of paraformaldehyde, 1.1 g. (0.014 mole) of pyridine, 0.83g. (0.0017m.) of titanium cresylate, and 905 ml. of solvent. The results are shown in Table 8.

TABLE 8

| Example | Solvent | NSA Yield (%) |
| --- | --- | --- |
| 34 | Toluene | 58.4 |
| 35 | Chlorobenzene | 59.8 |
| 36 | 1,4-Dioxane | 32.3 |

EXAMPLES 37 AND 38

Toluene (630 ml) was charged to a two liter Parr Stirred Autoclave, model 4500, and heated to 213° C. The catalyst was prepared by refluxing 4.54g. (0.0095 mole) of titanium cresylate, 3.46g. (0.023 mole) of 8-hydroxyquinoline, and 8g. of toluene for 30 minutes. A portion (2.49g.) of the resultant catalyst mixture was then added to a slurry containing 0.60 mole of the alkyl phenol, 81.1 g. (2.57 moles @ 95%) of paraformaldehyde, and 50 ml. of toluene. The resultant slurry mixture was pumped into the reactor over a period of 5-30 minutes. An additional 200 ml. of toluene was then pumped into the reactor to insure complete transfer of all the reactants. After two hours at 213° C., the reactor was cooled and the contents worked up in the same fashion as described in Example 1. The resultant oils were assayed by either gas chromatography or high pressure liquid chromatography. The results of the two different alkylphenols are shown in Table 9. The dodecyl phenol was a commercially available phenol in which the dodecyl group is derived from tetrapropylene. The nonylphenol is the same as employed in the earlier examples above.

TABLE 9

| Example | Alkylphenol | Product | Yield % |
| --- | --- | --- | --- |
| 37 | Nonylphenol | Nonylsalicylaldehyde | 68.3 |
| 38 | Dodecylphenol | Dodecylsalicyladehyde | 68.1 |

EXAMPLE 39

In this example commercially available octylphenol was employed. The procedure was carried out in the same manner as in Example 1 except that nonylphenol was replaced with 137.6g. (0.668 mole) of octylphenol. The yield of octylsalicylaldehyde was 66%.

EXAMPLE 40 TO 44

The examples illustrate the use of other phenols. The procedure was carried out in the same manner as in Example 2, except that nonylphenol was replaced by the phenols shown in the Table 10, and the pyridine was added as a portion of the slurry. The crude products were assayed by nuclear magnetic resonance.

TABLE 10

| Example | Phenol | Phenol wt. (g.) | Aldehyde Yield (%) |
| --- | --- | --- | --- |
| 40 | Phenol | 62.8 | 45.7 |
| 41 | p-Chlorophenol | 85.5 | 41.4 |
| 42 | p-tert-butylphenol | 100 | 68.0 |
| 43 | o-tert-butylphenol | 100 | 98.0 |
| 44 | p-methoxyphenol | 82.8 | 63.3 |

EXAMPLE 45

The procedure was carried out in the same fashion as described for example 38 except that the catalyst was prepared by stirring 0.51g.(0.0018 mole) of titanium(IV) butoxide, 0.54g.(0.0037 mole) of 8-hydroxyquinoline, and 1.0g. of toluene together for 30 minutes. The resultant catalyst mixture was then transferred quantitatively into the slurry. The yield of dodecylsalicylaldehyde was 71.5%.

EXAMPLES 46 and 47

The procedure was carried out in the same fashion as described for Example 37 except that 8-hydroxyquinoline was replaced on a mole for mole basis by the chelating agent listed in Table 11.

TABLE 11

| Example | Chelating Agent | NSA Yield (%) |
| --- | --- | --- |
| 46 | 4-t-Butyl catechol | 52.5 |
| 47 | Tropolone | 46.0 |

EXAMPLES 48 AND 49

Toluene (630 ml.) was charged to a two liter Parr stirred autoclave, model 4500, and heated to 225° C. Catalyst A was prepared by refluxing 4.54g.(0.0095 mole) of titanium cresylate, 3.46g.(0.023 mole) of 8-hydroxyquinoline and 8g. of toluene for 30 minutes. Catalyst B was prepared by stirring 4.54g.(0.0095 mole) of titanium cresylate, 6.59g.(0.023 mole @ 92% purity) of nonylsalicylaldoxime, and 8g. of toluene for one hour. A portion of the resultant catalyst mixture (see Table 12) was then added to a slurry containing 144.9g.(0.65 mole) of nonylphenol, 67.47g.(2.14 mole @ 95% purity) of paraformaldehyde, 2.1 g.(0.026 mole) of pyridine, and 50 ml. of toluene. The resultant slurry mixture was then pumped into the reactor over a 5 minute interval. An additional 200 ml. of toluene was then pumped into the reactor to insure complete transfer of all the reactants. After two hours at 225° C., the reactor was cooled and the contents worked up in the same fashion as described in Example 1. The resultant oils were assayed by gas chromatography.

TABLE 12

| Example | Catalyst | Weight (g.) | NSA Yield (%) |
| --- | --- | --- | --- |
| 48 | A | 6.26 | 68.3 |
| 49 | B | 7.84 | 41.5 |

EXAMPLES 50 THROUGH 52

Toluene (850ml.) was charged to a two liter Parr stirred autoclave, model 4500, and heated to 180° C. A slurry containing 100g(0.45 mole) of nonylphenol, 43g.(1.36 mole @ 95%) of paraformaldehyde, 2.1 g.(0.026 mole) of pyridine, 50ml. of toluene, and sufficient catalyst to provide 0.0038 mole of titanium was then pumped into the reactor over a five minute period. An additional 200 mls of toluene was then pumped into the reactor to insure transfer of all the reactants into the reactor. After two hours at 180° C., the reactor was cooled. The reactor contents were then worked up and assayed as described for Examples 15 through 19. The results are summarized in Table 13.

TABLE 13

| Example | Catalyst | Weight (g.) | NSA Yield (%) |
|---|---|---|---|
| 50 | Cresyl polytitanate | 1.95 | 55.3 |
| 51 | Octylene glycol titanate | 2.28 | 55.1 |
| 52 | Isopropyl tricumylphenyl titanate | 2.79 | 61.4 |

EXAMPLES 53 AND 54

The procedure was carried out in the same manner as in Example 15 except that the charge was modified. In one case, nonylsalicylaldehyde (46.4g.,0.10 mole) was added to the charge. The charge contained 110g.(0.5 moles) of nonylphenol, 47.47g. (1.50 mole @ 95%) of paraformaldehyde, 2.1 g. (0.026 mole) of pyridine, 1.8g.(0.0038 mole) of titanium cresylate, and one liter of toluene. The results are summarized in Table 14.

TABLE 14

| Example | NSA Yield (%) |
|---|---|
| 53 | 56 |
| 54* | 65 |

While the invention has now been described in terms of various preferred process parameters, and exemplified with respect thereto, the skilled artisan will appreciate that various substitutions, changes, omissions, and modifications may be made without departing from the spirit thereof. Accordingly, it is intended that the scope of the invention be limited solely by that of the following claims.

The embodiments of the present invention in which an exclusive property or privilege is claimed are defined as follows:

1. In a process of preparing an hydroxyarylaldehyde wherein a phenolic compound is reacted with formaldehyde in the presence of a solvent and a catalyst, the improvement wherein said catalyst is an organic moiety containing titanium (IV) or zirconium (IV) compound.

2. A process as described in claim 1 wherein said catalyst is selected from the groups consisting of alkyl, alkaryl, aryl, aralkyl titanates, titanium acylates, titanium halides, titanium chelates and titanate polymers.

3. A process as defined in claim 2 wherein said alkyl group contains from 1-22 carbon atoms and said aryl group is phenyl.

4. A process as defined in claim 1 wherein said catalyst is a titanium compound having the formula (M)W,X,Y,Z,   I wherein M represents titanium or zirconium and any one of W,X,Y and Z, which may be the same or different, is selected from the group of halogen, alkoxy, aryloxy, alkaryloxy, aralkoxy and acyloxy, and cyclopentadienyl or residues of a β-diketone, an 8-hydroxyquinoline or a salicylaldehyde and in which any two of W,X,Y,Z, together may be oxide, provided that when any two are the oxide, the remaining two are selected from the groups of halogen, alkoxy, aryloxy, alkaryloxy, aralkoxy and a residue of a β-diketone, salicylaldehyde or an 8-hydroxyquinoline, or II:

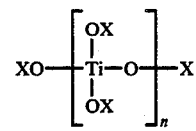

where n is an integer representing the number of repeating units and where X, which may be the same or different, is alkyl, aryl, alkaryl, aralkyl or a residue of a β-diketone, salicylaldehyde or an 8-hydroxyquinoline.

5. A process as defined in claim 4 wherein said alkyl group has from 1 to 22 carbon atoms.

6. A process as defined in claim 4 wherein said aryl group is phenyl.

7. A process as defined in claim 4 wherein said halogen is Cl.

8. A process as defined in claim 4 wherein said β-diketone is 2,4-pentanedione.

9. A process as defined in claim 4 wherein said hydroxy quinoline is 8-hydroxyquinoline.

10. A process as defined in claim 4 wherein said salicylaldehyde is an alkylsalicylaldehyde wherein said alkyl group contains 8-12 carbon atoms.

11. A process as defined in claim 4 wherein said salicylaldehyde is nonylsalicylaldehyde.

12. A process as defined in claim 4 wherein the salicylaldehyde is the salicylaldehyde prepared in the process.

13. A process as defined in claim 1, wherein said catalyst is selected from the group consisting of:
Titanium(IV) cresylate
Octylene glycol titanate
Triethanolamine titanate
Titanium(IV) diisopropoxide bis(2,4-pentanedionate)
Titanium(IV) oxide bis(2,4-pentanedionate)
Titanium tetrachloride
Bis(cyclopentadienyl)titanium dichloride
Isopropyl triisostearoyl titanate
Isopropyl tricumylphenyl titanate
Isopropyl tri(N-ethylamino-ethylamino) titanate
Isopropyl tri(2-aminobenzoyl) titanate
Tetraisopropyl di(dioctylphosphito) titanate
Zirconium(IV) 2,4-pentanedionate
Titanium(IV) butoxide
Zirconium(IV) butoxide
Cresyl polytitanate.

14. A process defined in claim 1 wherein said catalyst is a reaction product of a titanate ester and a complexing compound selected from the group consisting of salicylaldehydes, 8-hydroxyquinoline and 2,4-pentanedione.

15. A process as defined in claim 14 wherein said product is preformed and prepared by reacting said ester and said complexing compound.

16. A process as defined in claim 14 wherein said titanate ester is titanium(IV) cresylate.

17. A process as defined in claim 14 wherein said titanate ester is titanium(IV) butoxide.

18. A process as defined in claim 1 wherein a catalyst promoter is employed along with said catalyst.

19. A process as defined in claim 6 wherein said promoter is an unhindered aromatic amine.

20. A promoter as defined in claim 7 wherein said amine is pyridine.

21. A process as defined in claim 1 wherein said catalyst is employed in an amount of about 0.005 to 0.0005 moles per mole of phenolic compound.

22. A process as defined in claim 1, wherein said catalyst is employed in an amount of 0.017 to 0.0005 moles per mole of phenolic compound.

23. A process as defined in claim 1 wherein said reaction is conducted at a temperature in the range of about 150°–250° C.

24. A process as defined in claim 1 wherein said reaction is conducted at a temperature in the range of about 180°–220° C.

25. A process as defined in claim 1 wherein paraformaldehyde is employed to provide the formaldehyde.

26. A process as defined in claim 1 wherein said formaldehyde is employed is a molar ratio of formaldehyde to phenolic compound of about 2–6.

27. A process as defined in claim 26 wherein said formaldehyde is employed in a molar ratio of 3–5.

28. A process as defined in claim 1 wherein said phenolic compound is a phenol having at least one unsubstituted ortho-position available for reaction.

29. A process as defined in claim 1 wherein said phenolic compound has the formula

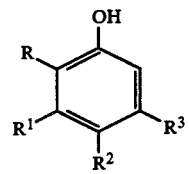

wherein $R, R^1, R^2$ and $R^3$, which may be the same or different, represent a hydrogen atom; an alkyl, aryl, alkaryl, aralkyl, or cycloalkyl group; an alkoxy, aryloxy or acyl group; or a halogen.

30. A process as defined in claim 29 wherein said alkyl group contains from 1–22 carbon atoms and said aryl group is phenyl.

31. A process as defined in claim 1 wherein said phenolic compound is selected from the group consisting of octylphenol, nonylphenol and dodecylphenol.

32. A process for preparinig an orthohydroxybenzaldehyde which comprises reacting a phenolic compound which is unsubstituted in the ortho position with paraformaldehyde which reaciton takes place in the presence of a catalytic amount of an organic moiety containing titanium IV compound, an inert solvent and pyridine.

* * * * *